United States Patent [19]

Liauw et al.

[11] 4,282,166

[45] Aug. 4, 1981

[54] PREPARATION OF LOWER TRIALKYLTIN HYDRIDE FROM TRIALKYLTIN CHLORIDE

[75] Inventors: Koei-Liang Liauw, Wyckoff; Michael H. Fisch, Wayne, both of N.J.

[73] Assignee: Argus Chemical Corporation, Brooklyn, N.Y.

[21] Appl. No.: 139,601

[22] Filed: Apr. 11, 1980

[51] Int. Cl.³ ............................................... C07F 7/22
[52] U.S. Cl. .................................................. 260/429.7
[58] Field of Search ...................................... 260/429.7

[56] References Cited

U.S. PATENT DOCUMENTS

| | | | |
|---|---|---|---|
| 3,281,443 | 10/1966 | Hunt | 260/448 AD |
| 3,347,891 | 10/1967 | Neumanu et al. | 260/429.7 |
| 3,379,747 | 4/1968 | Itoi | 260/429.7 |
| 3,439,010 | 4/1959 | Okawara et al. | 260/429.7 |
| 3,507,895 | 4/1970 | Casensky et al. | 260/448 AD |
| 3,758,620 | 9/1973 | Vit | 260/448 AD X |

OTHER PUBLICATIONS

Chemical Abstracts, 55 27809h, (1967).
Finholt et al., JACS 69 2692–2696, (1947).
Vit et al., Eastman Organic Chemical Bulletin, vol. 46, No. 1, p. 5, (1974).
Fish et al., JACS 89 5861, (1967).

Primary Examiner—Helen M. S. Sneed
Attorney, Agent, or Firm—Albert L. Gazzola; Morton Friedman

[57] ABSTRACT

A simple, direct, and safe process for preparing an organic solvent solution of a lower trialkyltin hydride of high purity and in high yield by reacting a lower trialkyltin chloride with an alkali metal bis(2-alkoxyethoxy)aluminum dihydride in a hydrocarbon solvent boiling in the 50° to 200° C. range.

10 Claims, No Drawings

PREPARATION OF LOWER TRIALKYLTIN HYDRIDE FROM TRIALKYLTIN CHLORIDE

FIELD OF THE INVENTION

This invention relates to a new process for preparing a lower trialkyltin hydride, having a total of no more than 12 carbon atoms, and having no more than 8 carbon atoms on any alkyl group.

Trialkyltin hydrides have long been known, but their use for synthetic purposes is relatively recent. G. Van der Kerk et al. in Journal of Applied Chemistry 1957, vol. 7, pages 356–365 found that trialkyltin hydrides can enter into addition reactions with olefins resulting in the formation of tin-carbon bonds, subsequently termed "hydrostannation" reaction:

$$R_3SnH + CH_2:CHR' \rightarrow R_3Sn-CH_2-CH_2R'$$

In another reaction of trialkyltin hydride, termed "hydrostannolysis" trialkyltin hydride acts as a selective reducing agent breaking a specific bond in a molecule and replacing it by a bond to metal or to hydrogen:

$$R_3SnH + \phi \rightarrow R_3Sn + \phi H$$

$$R_3Sn + R'X \rightarrow R_3SnX + R'.$$

$$R' + R_3SnH \rightarrow R_3Sn + R'H \text{ etc.}$$

where $\phi$ is an initiator fragment radical.

As a result, interest in reactions of trialkyltin hydrides increased and useful industrial products of such reactions were developed. For example, certain hydrostannation products of unsatruated sulfones are described by R. Strunk et al. in U.S. Pat. No. 3,976,672 of Aug. 24, 1976 to be effective in controlling insects, mites, and aphids.

PRIOR ART

A. E. Finholt et al. in J. Amer. Chem. Soc. 194, vol. 69, p. 2692–6 disclose a general method for preparation of hydrides of fourth main group elements and their organic derivatives. The method involves the action of lithium aluminum hydride on the appropriate halide wherein the halogen atoms are replaced by hydrogen and wherein the authors use diethyl ether or 1,4-dioxane as solvents. Preparation of trimethyltin hydride is mentioned, but no solvents, reaction conditions, work-up methods, or yields are given. In preparations, the products are volatile at 25° C. and handled by high vacuum techniques applicable only to small scale work.

G. Van der Kerk et al. in J. Applied Chemistry, 1957, vol. 7, p. 366–369 shows the preparation of triethyltin hydride, tri-n-propyltin hydride, and tri-n-butyltin hydride by reaction of equimolar quanities of the corresponding chloride and lithium aluminum hydride in boiling diethyl ether. Based on the reaction equation shown in Finholt, supra this is a 300% excess of lithium aluminum hydride. The hydride products were recovered in 66 to 75% of theoretical yields after quenching the reaction product in water, ether extraction, drying, solvent removal, and distillation.

R. Fish et al. in J. Amer. Chem. Soc. 1967, vol. 89, p. 5861 describes the preparation of trimethyltin hydride from trimethyltin chloride and lithium aluminum hydride in bis(2-ethoxyethyl)ether in 87% yield when 100% excess over theoretical lithium aluminum hydride is used.

K. Itoi in U.S. Pat. No. 3,379,747 of Apr. 23, 1968 discloses the preparation of tri-n-butyltin hydride from bis (tri-n-butyltin) oxide by reaction with a silicon hydride such as trimethylsilane or methyl hydrogen polysiloxane. Itoi describes the yield as quantitative but acknowledges the presence of silicon bearing impurities in his product.

E. Birnbaum et al. in Inorganic Syntheses 1970, vol. 12, p. 45–49 and 52–53 shows the reduction of trimethyltin chloride and tri-n-butyltin chloride to trimethyltin hydride and tri-n-butyltin hydride respectively with sodium borohydride in a glycol ether solvent under chilled conditions. Birnbaum theoretically requires one mole of sodium borohydride per mole of trialkyltin chloride which generates one equivalent (0.5 mole) of diborane, a highly toxic and spontaneously flammable gas. To prevent evolution of diborane during the reaction, Birnbaum et al. uses a considerable excess of sodium borohydride which holds the by-product diborane in solution as a complex. In the subsequent recovery of the organotin hydride, however, the diborane must be volatilized from the reaction mixture and must be trapped in a liquid nitrogen chilled receiver at −196° C., after which it is destroyed by reaction with a large excess of acetone.

R. Sommer et al. in J. Organic Chemistry 1968, vol. 33, p. 802–805 discloses a preparation of trimethyltin hydride from trimethyltin chloride and tri-n-butyltin hydride by a hydride interchange reaction. In the absence of a practical method for preparing the latter hydride the interchange reaction is merely of academic interest.

J. Vit et al. in Eastman Organic Chemical Bulletin, 1974, vol. 46, No. 1, page 5 discloses a dehalogenation of tributyltin chloride with VITRIDE reducing agent (sodium bis (2-methoxyethoxy) aluminum hydride) in boiling diethyl ether. After a workup procedure including water quenching, ether extraction, drying, evaporation and distillation, substantially as shown by Van der Kerk supra, for the use of lithium aluminum hydride, 45.5% yield of tributyltin hydride is obtained. Although by this method tributyltin chloride is successfully reduced to the hydride, the yield is low and it calls for the use of diethyl ether which is notoriously volatile, flammable and explosive. The yield is so low as to render impractical, by this route, many interesting processes which involve the use of the expensive organotin halides.

It is seen that the known methods of preparing lower trialkyltin hydrides require many separation and handling steps and are not well suited to the containment and safe handling of toxic and flammable starting materials, intermediates, and by-products. Moreover, the known methods are inefficient and wasteful in the use of costly reagents and special solvents, and sometimes give poor yields; the known methods are also difficult if not impossible to scale up beyond laboratory quantities of the lower trialkyltin hydrides. A need therefore exists for a safe process for manufacturing lower trialkyltin hydrides on an industrial scale.

SUMMARY OF THE INVENTION

We have discovered a process for preparing an organic solvent solution of a lower trialkyltin hydride in high yield and purity, with a minimum of handling steps and occasions for persons to be exposed to hazardous materials. The present process comprises reacting a lower trialkyltin chloride with an alkali metal bis(2-alkyoxyethoxy)aluminum dihydride in the presence of a hydrocarbon solvent boiling in the 50° to 200° C. range, whereby a solution of the lower trialkyltin hydride is obtained, which hydride is conveniently utilized, in solution as a reactant in an addition reaction ("hydrostannation") or as a reducing agent of controlled activity ("hydrostannolysis"), as hereinbefore described.

The reaction of trialkyltin chloride with a slight excess of alkali metal bis(2-alkoxyethoxy)aluminum dihydride proceeds rapidly under mild conditions. Suprisingly, large excesses of the aluminum dihydride reagent are deleterious and in the extreme case lead to complete destruction of the desired product. Furthermore, it is an advantage of the present process that the lower trialkyltin hydride produced can be readily separated by distillation from unchanged trialkyltin chloride starting material, so that it is quite practical to operate with a deficiency of aluminum dihydride reagent in each of several successive treatments of a quantity of trialkyltin chloride until all of the latter is converted.

The proportions of alkali metal bis(2-alkoxyethoxy) aluminum dihydride to trialkyltin chloride in the present process suitably range from 0.3 mole to 1 mole of the former per mole of the latter, preferably from 0.55 to 0.75 mole per mole. Thus, it is more efficient in the use of hydride reagent than prior art processes that require in theory at least one mole of hydride reagent, per mole of trialkyltin chloride, but in practice, a considerable excess over this amount.

DESCRIPTION OF PREFERRED EMBODIMENTS

Trialkyltin hydrides that can be prepared conveniently by process of this invention are the lower trialkyltin hydrides having from 1 to about 8 carbon atoms in the alkyl groups, which can be the same or different, and having a total of not more than 12 carbon atoms. Trialkyltin hydrides having more than 12 carbon atoms can be formed by the reaction of alkali metal bis(2-alkoxyethoxy) aluminum dihydride, but recovery from the reaction mixture becomes increasingly difficult as the carbons increase above 12. Accordingly, trialkyltin hydrides that can be prepared include trimethyltin hydride, triethyltin hydride, ethyldimethyltin hydride, tri-n-propyltin hydride, tri-isopropyltin hydride, methyl di-n-propyltin hydride, tributyltin hydride, tri-isobutyltin hydride, isobutyl dimethyltin hydride, ethyldi-n-butyltin hydride, diexthyl-n-hexyltin hydride, and dimethyl-n-octyltin hydride. Trimethyltin hydride and tri-n-butyltin hydride are particularly preferred. The required trailkyltin chloride starting materials are mostly known compounds; any that have not been described can be made by generally applicable methods.

The alkali metal bis(2-alkoxyethyl)aluminum dihydride has from 1 to about 6 carbon atoms in the alkoxy group. There can be used, for example, any of the sodium alkoxyethoxy-aluminum hydrides disclosed by J. Vit et al. in Czech Pat. No. 140,864 of Apr. 15, 1971, and in U.S. Pat. No. 3,507,895 of Apr. 21, 1970, as well as the analogous potassium and lithium compounds. Sodium bis(2-methoxyethoxy)aluminum dihydride, being commercially available, is particularly preferred.

The hydrocarbon solvent used in the present process represents at least 5% by volume of the mixture of reactants and solvent. Amounts in ecxess of about 90% by volume of the mixture, although useable, are wasteful and uneconomic. Solvent levels of 10% to 80% by volume are generally used and preferred.

Hydrocarbons as a class give the best results in our process and the presence of other kinds of solvents in substantial amounts is therefore undesirable. Accordingly, we use the term "solvent consisting essentially of hydrocarbon" to refer to solvents containing at least 95% by volume hydrocarbons and not more than 5% of other nonhydrocarbon materials. Solvents that can be used include aliphatic hydrocarbons such as hexane, heptane, isooctane, nonane, and "light petroleum" fractions within the indicated boiling range; cycloaliphatic hydrocarbons such as methylcyclopentane, cyclohexane, methylcyclohexane, menthane, alpha and beta pinenes, and turpentine mixtures; aromatic hydrocarbons such as benzene, toluene, xylene, ethylbenzene, cumene, and cymene. Toluene and xylene are particularly preferred.

In the operation of this process, the reactants and solvent can be admixed in any desired order, but it is preferred to add the alkali metal bis(2-alkoxyethoxy) aluminum dihydride, suitably diluted with a portion of hydrocarbon solvent, to the trialkyltin chloride reactant which can be neat or also diluted with hydrocarbon solvent. The reaction tends to be exothermic and is suitably moderated by cooling; it takes place as low as −10° C. but need not be kept that cold. Temperatures in the range from about 10° C. to about 110° C. are suitable; a particularly preferred range is from 20° to 60° C.

After reaction, which can range from a few minutes to several hours, the solution of trialkyltin hydride is recovered in one of several ways such as filtration, or solvent distillation. When tributyltin hydride, for example, is prepared for use in certain hydrostannation reactions with activated olefins or certain hydrostannolysis reactions, it is sufficient to remove sodium chloride and other solid reaction products that do not contain tin, by filtration, and utilize the filtrate in the next operation as source of tributyltin hydride. A specific instance of the hydrostannolysis reaction to which this process is well suited is the hydrostannolysis of trimethyltin chloride with tributyltin hydride in hydrocarbon solution obtained from the present process; the latter hydride can be used without purification, even if some tributyltin chloride is still present. After the hydrostannolysis reaction of trimethyltin chloride, the trimethyltin hydride product can be recovered by distillation, preferably as a solution in hydrocarbon solvent that distills at the same time, and the residue of tributyltin chloride reconverted to tributyltin hydride.

Distillation of lower trialkyltin hydride product is a particularly preferred recovery technique since these trialkyltin hydrides are distillable and readily separated from the corresponding trialkyltin chloride starting materials. In order to maximize ease of handling and minimize the exposure hazards of highly concentrated trimethyltin hydride and triethyltin hydride, these hydrides are conveniently recovered by distillation together with a close boiling solvent such as toluene or xylene. Solutions of trimethyltin hydride and triethyltin hydride in these solvents are conveniently obtained in any desired concentration and well suited for shipment, storage, and use.

The following Examples are provided to illustrate the process of this invention and are not intended to be limiting. For the sake of brevity, the term "Reagent B" is used to refer to a commercially available nominally 70% solution of sodium bis(2-methoxyethoxy)aluminum dihydride in benzene, having a 1.034 g/ml density at 20° C. and 280 ml volume corresponding to one mole, and the term "Reagent T" is used to refer to a commercially available nominally 70% solution of sodium bis-(2-methoxyethoxy)aluminum dihydride in toluene, having a 1.040 g/ml density at 20° C. and a 278 ml volume corresponding to one mole.

EXAMPLE I

An N.M.R. tube was charged with 0.25 ml of a 23% solution of trimethyltin chloride in toluene. 0.25 ml of Reagent B was added and the tube closed, kept at 25° C., and periodically examined in an N.M.R. spectrophotometer for the appearance of new bands. The doublet in the methyl group region at 0.1–0.2 ppm and the multiplet in the hydride group region at 4.5–4.7 ppm characteristic of trimethyltin hydride appeared clearly after a few minutes at 25° C.

In a comparison experiment, sodium diethyl aluminum dihydride (25% solution in toluene) was used instead of sodium bis (2-methoxyethoxy) aluminum dihydride under otherwise identical conditions. Two days were required for the appearance of a small band in the tin hydride region, and the characteristic doublet in the methyl group region did not appear.

These results show the critical nature of the sodium bis (alkoxyethyl) aluminum dihydride reagent in the production of trimethyltin hydride according to this invention.

EXAMPLE II

A 250 ml 3 necked flask equipped with a stirrer, an addition funnel, and a condenser connected to a trap cooled with solid $CO_2$ was charged with 10.4 ml Reagent B. The flask was chilled in a bath of water and ice for 15 minutes, and 53.6 g of a 23.1% solution of trimethyltin chloride in toluene was added through the dropping funnel during 15 minutes. The cooling bath was removed and the reaction mixture stirred a further 30 minutes. NMR analysis showed the presence of trimethyltin hydride product and remaining trimethyltin chloride starting material. Continued stirring for 3 hours at room temperature produced no change in this analysis.

The reaction mixture was then distilled under atmospheric pressure, giving a 9.5 g distillate boiling at 74° to 98° C. and containing 40.8% trimethyltin hydride along with benzene and toluene, as determined by NMR analysis, along with a trace of a second organotin compound believed to be hexamethyldistannane. The residue from the distillation contained trimethyltin chloride and no trimethyltin hydride. Accordingly, the yield of trimethyltin hydride in this preparation was 3.9 g, 38% of theoretical based on trimethyltin chloride charged, and over 90% based on trimethyltin chloride reacted.

The results of this example show the successful preparation and recovery of trimethyltin hydride according to this invention by reaction of trimethyltin chloride with sodium bis (2-methoxyethoxy) aluminum dihydride in a hydrocarbon solvent and clean separation from unchanged starting material by simple distillation.

EXAMPLE III

To the entire residue from the distillation in Example 2 at room temperature was added 11 ml of Reagent B in one portion. The mixture became lukewarm and was stirred for one hour without heating and then distilled under atmospheric pressure. There distilled an 18.3 g portion boiling at 69° to 100° C. and containing by NMR analysis 35.6% trimethyltin hydride, along with benzene and toluene but with no detectable hexamethyldistannane, and a subsequent 16.3 g portion boiling at 100° to 105° C. containing only a trace of trimethyltin hydride. Accordingly, the yield of trimethyltin hydride in this preparation was 6.5 g, which taken together with the 3.9 g obtained in Example 2 is close to quantitative conversion of the trimethyltin chloride charged to trimethyltin hydride.

The results here show the more efficient utilization of the sodium bis (2-methoxyethoxy) aluminum dihydride reagent and suppression of hexamethyldistannane byproduct obtained by adding the reagent to trimethyltin chloride according to this invention.

EXAMPLE IV

A solution of 54.2 g trimethyltin chloride in 40 ml toluene was charged to a reaction apparatus similar to that of Example 2, and 84 ml Reagent B diluted with 40 ml toluene was added during 15 minutes while keeping the temperature at 24°–28° C. by external cooling. After the addition the cooling was stopped and stirring continued for 30 minutes. Analysis showed that there was still some unreacted trimethyltin chloride, and a further quantity of Reagent B (8 ml diluted with 10 ml toluene) was added to the mixture at 28°–30° C. After a further 30 minute reaction period, the mixture was distilled as in Example 3, giving 71.4 g distillate boiling 63° to 98° C. and containing 50.1% trimethyltin hydride, which represents 79.9% yield based on the trimethyltin chloride charged.

Since the distillation residue contained unreacted trimethyltin chloride, addition of Reagent B and distillation after a 30 minute reaction period were repeated twice more, giving distillates containing additional 6 g and 3.2 g quantities of trimethyltin hydride for a nearly 100% conversion of starting material to trimethyltin hydride. The total amount of Reagent B added during the four steps was 136 ml, or 1.79 mole per mole of trimethyltin chloride.

EXAMPLE V

An apparatus as in Example 2 was charged with 65.1 g tributyltin chloride (95% minimum assay) diluted with 40 ml toluene. During 30 minutes there was added 35 ml Reagent T, with the temperature rising to 42° C. Stirring was continued for 1 hour after addition of the reagent.

Next, the toluene was stripped under reduced pressure, and the product distilled to give 54.3 g (93.3% of theoretical yield) tributyltin hydride, b.p. 105°–108° C./5 mm. The results show the preparation of tributyltin hydride in excellent yield by a process according to this invention.

EXAMPLE VI

An apparatus similar to that in Example 2 was charged with 205 g tributyltin chloride and 50 ml toluene. During 35 min. there was added 110 ml Reagent T with the temperature controlled at 30° C. maximum by ice bath cooling. An hour after complete addition the toluene was distilled off. The residue, including a considerable amount of solid, was distilled under vacuum to give 179.5 g crude tributyltin hydride boiling 102°–110° C./5 mm. This was redistilled to give 158.9 g boiling 104°–106° C./5 mm and 8.0 g boiling 106°–116° C./5 mm, both showing only tributyltin hydride in the NMR spectrum, and a 12.5 g residue having the NMR spectrum of tributyltin chloride, for a 91.1% of theoretical yield of tributyltin hydride based on tributyltin chloride charged.

The results of this example show the preparation of tributyltin hydride in excellent yield and purity by a process according to this invention.

EXAMPLE VII

A one liter apparatus similar to that of Example 2 was charged with 162 g tributyltin chloride. During 20 minutes 87.3 ml Reagent T was added while keeping the temperature at 28°–30° C. by using an ice-water bath. The mixture was then heated at 45°–50° C. for 30 minutes and filtered. The filtrate was stripped of toluene under reduced pressure and distilled to give 137.6 g (95% of theoretical yield) tributyltin hydride, boiling 118°–124° C. at 5 to 6 mm. A 15 g portion of the tributyltin hydride was mixed with 26.6 g trimethyltin chloride solution (38.6% in toluene) and distilled immediately. The distillate boiling up to 110° C. weighed 17.9 g and consisted, according to NMR analysis, of 46.8% trimethyltin hydride and 53.2% toluene. Thus the contained trimethyltin hydride (8.5 g) represents a 98.8% of theoretical yield based on trimethyltin chloride and a 93.9% of theoretical yield for the two stages of tributyltin chloride reduction to tributyltin hydride according to this invention and transposition to trimethyltin hydride and tributyltin chloride for recycle to the process. Inclusion of the hydride exchange reaction enables the relatively small losses of organotin species during the reduction step to be borne by the commercially available and less toxic tributyltin, thus economizing and minimizing exposure to the less available trimethyltin.

EXAMPLE VIII

A 5 liter reaction apparatus kept under nitrogen to exclude air was charged with 1402 g of a 53.3% solution of trimethyltin chloride in toluene. During 1 hour there was added 578 ml Reagent T diluted with 300 ml toluene with the temperature kept at 25° maximum. After complete addition the mixture was distilled to give 937.4 g distillate boiling 53°–110° C. and containing 54.4% (509.9 g) trimethyltin hydride. The residue was treated with 52 ml Reagent T and 30 ml toluene at 35°–40° C. and again distilled, giving 194.5 g distillate boiling 95°–110° C. and containing 18.5 % (36 g) trimethyltin hydride, thus resulting in a total 88.1% of theoretical yield of trimethyltin hydride. The total quantity of Reagent T used was 2.27 moles of sodium bis (2-methoxyethoxy) aluminum dihydride, which represents 0.6 mole per mole of trimethyltin chloride charged or 0.68 mole per mole of trimethyltin hydride produced.

These results demonstrate the remarkable efficiency of the production of trimethyltin hydride according to this invention.

EXAMPLE IX

A 500 ml apparatus similar to that in Example 2 was charged with 74.6 g trimethyltin chloride and 50 ml toluene. During 40 minutes there was added 211 ml of Reagent B diluted with 40 ml toluene. The temperature ranged from 40° to 51° C. About 15 minutes after complete addition the product was distilled under atmospheric pressure. At this point the reaction mixture was yellow, having been water white to start.

Gas evolved throughout the distillation that failed to condense in a cold trap. Distillate temperature rose from 28° to 76° and then dropped to 61° C. while 60.9 g distillate was collected. On continued distillation, 3.3 g were obtained while the distillate temperature dropped from 60° to 55° C.; at this point the distillation was stopped. A further 3.3 g of condensate was found in the cold trap. All three overhead fractions had the same NMR spectrum which was different from that of trimethyltin hydride.

This experiment shows that when an excessive proportion here 2.01 mole per mole trimethyltin chloride of sodium bis (2-methoxyethxy) aluminum dihydride is used in a single operation, trimethyltin hydride is not obtained.

We claim:

1. A process for preparing an organic solvent solution of a lower trialkyltin hydride, comprising reacting a lower trialkyltin chloride with an alkali metal bis(2-alkoxyethoxy)aluminum dihydride in the presence of a solvent, said solvent consisting essentially of hydrocarbon boiling in the 50° to 200° C. range, whereby lower trialkyltin hydride is obtained.

2. A process according to claim 1 in which the lower trailkyltin hydride is trimethyltin hydride.

3. A process according to claim 1 in which the lower trialkyltin hydride is tributyltin hydride.

4. A process according to claim 1 in which the alkali metal bis(2-alkoxyethoxy)aluminum dihydride is sodium bis(2-methoxyethoxy)aluminum dihydride.

5. A process according to claim 1 in which the solvent is toluene.

6. A process according to claim 1 in which the quantity of alkali metal bis(2-alkoxyethosy)aluminum dihydride is in the range from 0.3 1 mole per mole of lower trialkyltin chloride.

7. A process according to claim 6 in which the quantity of alkali metal bis(2-alkoxyethoxy)aluminum dihydride is in the range from 0.55 to 0.75 mole per mole of lower trialkyltin chloride.

8. A process according to claim 1 in which the lower trialkyltin hydride is recovered by distillation.

9. A process according to claim 8 in which the lower trialkyltin hydride is trimethyltin hydride.

10. A process according to claim 1 in which the lower trialkyltin hydride obtained is caused to react in the presence of hydrocarbon solvent with a second lower trialkyltin chloride, whereby a solution of the trialkyltin hydride whose alkyl groups correspond to the second trialkyltin chloride is recovered.

* * * * *